United States Patent [19]
Roduit et al.

[11] Patent Number: 5,614,636
[45] Date of Patent: Mar. 25, 1997

[54] PROCESS FOR THE PREPARATION OF 2,4-PYRIDINE DICARBOXYLIC ACID

[75] Inventors: Jean-Paul Roduit, Sierre; Alain Wellig, Ried-Mörel; Karin Amacker, Eischoll; Martin Eyer, Glis, all of Switzerland

[73] Assignee: Lonza Ltd., Gampel/Valais, Switzerland

[21] Appl. No.: 250,576

[22] Filed: May 27, 1994

[30] Foreign Application Priority Data

Jun. 1, 1993 [CH] Switzerland ............... 1630/93

[51] Int. Cl.$^6$ .................................. C07D 213/30
[52] U.S. Cl. .................. 546/327; 546/286; 546/317; 546/323
[58] Field of Search ................. 546/286, 317, 546/323, 327

[56] References Cited

U.S. PATENT DOCUMENTS 2,780,624  2/1957  Webb et al. ............... 544/406

FOREIGN PATENT DOCUMENTS

| 0068219 | 1/1983 | European Pat. Off. |
| 2056433 | 7/1971 | Germany. |
| 2539435 | 8/1977 | Germany. |

OTHER PUBLICATIONS

Wagner & Zook "Synthetic Organic Chemistry" John Wiley & Sons, Inc. pp. 168,416–417,666–667.

CA 92: 22525 b Kawamura et al. 1980.

Wagner & Zook Synthetic Organic Chemistry John Wiley & Sons. Inc. N.Y. 1953. pp. 415–417.

*Primary Examiner*—Jane Fan
*Attorney, Agent, or Firm*—Fisher, Christen & Sabol

[57] ABSTRACT

A process for the preparation of carboxamides of nitrogen-containing aromatic heterocyclic compounds from the corresponding N-heterocyclic compounds by reaction thereof with formamide in the presence of peroxodisulfuric acid or a peroxodisulfate.

17 Claims, No Drawings

PROCESS FOR THE PREPARATION OF 2,4-PYRIDINE DICARBOXYLIC ACID

BACKGROUND OF THE INVENTION

1. Field of the Invention

The invention relates to a new process for the preparation of carboxamides of nitrogen-containing aromatic heterocyclic compounds (N-heterocyclic compounds) and to the use of the carboxamides obtained for the preparation of the corresponding carboxylic acids by alkaline hydrolysis.

2. Background Art

Both the carboxamides and the carboxylic acids of N-heterocyclic compounds are important intermediate products for the preparation of pharmaceuticals. A carbamoylation method for N-heterocyclic compounds is known from German Patent No. 2,056,433. This process is distinguished by the fact that a redox system of R-OOH+iron(II) is used for formation of the carbamoyl radical. R here denotes hydrogen, alkyl or cycloalkyl. Iron(II) must be used here in stochiometric amounts or even in excess, which obviously results in major waste water and waste product problems in the case of syntheses on an industrial scale. The alkyl hydroperoxides used are expensive, and furthermore are hazardous to handle because of their explosiveness.

BROAD DESCRIPTION OF THE INVENTION

Because of the disadvantages described above, the main object of the invention is to provide a carbamoylation process which can be employed on an industrial scale and functions without the above-described deficiencies. The main object is achieved in a surprisingly simple manner by the carbamoylation process of the invention. Other objects and advantages of the invention are set out herein or are obvious herefrom to one skilled in the art.

The objects and advantages of the invention are achieved by the process of the invention.

The invention involves a process for the preparation of carboxamides of nitrogen-containing aromatic heterocyclic compounds. In the process, a nitrogen-containing aromatic heterocyclic compound is reacted with formamide in the presence of peroxodisulfuric acid or a peroxodisulfate.

Preferably the process is carried out in the presence of a peroxodisulfate, more preferably, ammonium peroxodisulfate. Preferably the peroxodisulfuric acid or the peroxodisulfate is employed in an amount of 1.1 to 3.0 mol per mol of N-heterocyclic compound employed. Preferably the formamide is employed in an amount of 5 to 35 mol per mol of N-heterocyclic compound employed. Preferably the reaction is additionally carried out in the presence of a strong acid. Preferably the reaction is carried out at a temperature between 20° to 80° C.

The invention further involves a process of using the carboxamides of nitrogen-containing aromatic heterocyclic compounds for the preparation of the corresponding carboxylic acids by alkaline hydrolysis.

DETAILED DESCRIPTION OF THE INVENTION

N-heterocyclic compounds are expediently understood as meaning compounds from the series comprising pyridines, quinolines, isoquinolines, pyrimidines, pyridazines, pyrazines, quinoxalines, quinazolines, acridines and benzimidazoles. These compounds can optionally carry one or more substituents from the series comprising alkyl, alkoxy, alkanoyl, alkoxycarbonyl, arylalkyl, aryloxycarbonyl, halogen, carboxyl, cyano, amino, alkylamino and dialkylamino. The alkyl groups occurring in the substituents mentioned are either linear or branched and expediently have 1 to 6 C atoms preferably 1 to 4 C atoms. An aryl group is expediently understood as meaning a phenyl group which is optionally substituted by the substituents mentioned above. Halogen usually represents fluorine, chlorine, bromine or iodine.

Formamide is expediently added in an amount of 3 to 35 mol, preferably in an amount of 5 to 6 mol, per mol of N-heterocyclic compound employed. Peroxodisulfuric acid or the peroxodisulfate is advantageously likewise metered into the mixture in a slight excess, that is to say, in an amount of expediently 1.1 to 3.0 mol per mol. The peroxodisulfates of peroxodisulfuric acid are advantageously preferred. Suitable peroxodisulfates are the readily accessible peroxodisulfate of sodium, potassium or ammonium.

To improve the selectivity of the carbamoylation, the reaction is advantageously carried out in the presence of a strong acid, preferably in the presence of sulfuric acid. The addition of a solvent is not essential, since in principle the formamide used in excess can assume this function. Nevertheless, it is possible to carry out the reaction in the presence of a polar inert solvent. Acetonitrile has proved to be particularly suitable.

The reaction temperature is expediently between 20° and 80° C., preferably between 65° and 75° C.

The resulting carboxamide can already be isolated from the reaction mixture in a manner known to the expert after a relatively short time after the addition of peroxodisulfuric acid or peroxodisulfate has ended. As a rule, the carboxamide is obtained in a good yield of greater than 80 percent and in a high purity.

Depending on the substitution of the N-heterocyclic compounds employed, two carboxamide functions can be introduced in the reaction according to the invention. This is the case in particular with "electron-donating" groups, such as, alkyl groups. The reaction according to the invention of 4-methylpyridine thus results in 4-methylpyridine-2,6-dicarboxamide.

The resultant carboxamides can be either isolated or hydrolyzed directly under alkaline conditions to give the corresponding carboxylic acids. If the carboxamides prepared according to the invention contain CN groups as substituents, these are as a rule likewise hydrolyzed to carboxylic acid. Alkaline hydrolysis of the 4-cyano-2-pyridinecarboxamide prepared from 4-cyanopyridine thus results in pyridine-2,4-dicarboxylic acid, which is important as an intermediate product for pharmaceuticals.

EXAMPLE 1

(a) Process for the preparation of 4-cyano-2-pyridine-carboxamide 85 g (0.82 mol) of 4-cyanopyridine was initially introduced into 700 ml of acetonitrile at room temperature. 32.4 g (0.32 mol) of 98 percent strength sulfuric acid were then added. The resultant white suspension was heated to 60° C., after which 201.3 g (4.47 mol) of formamide in 52 g of water was added. The resulting clear solution was heated to 70° C., after which 281.3 g (1.23 mol) of ammonium peroxodisulfate was metered into the solution in portions over a period of 2 hours (exothermicity). When the addition had ended, stirring was continued at 74° C. for 75 minutes, 880 ml of water was then added and the water/acetonitrile azeotrope was distilled off in vacuo. The white-yellow suspension was then filtered at 80° C. and the filter cake was washed with water heated to 80° C. and dried in vacuo. 117 g (87.5 percent) of the title product was obtained with a content of about 90 percent (HPLC).

(b) Process for the preparation of pyridine 2,4-dicarbboxylic acid 80 g (0.5 mol) of 4-cyano-2-pyridinecarboxamide was suspended in 155 ml of water. 170.3 g of 30 percent strength sodium hydroxide solution was then added dropwise at 80° C. in the course of 30 minutes, after which a yellow solution was formed. After the solution had been stirred for 30 minutes, it was brought to pH 1.5 with concentrated hydrochloric acid, the resultant white suspension was cooled and filtered and the filter cake was washed with water. Thereafter, the filter cake was suspended again in water, the pH was brought to 1 with hydrochloric acid and the solid was dissolved at 95° C. When subsequently allowed to cool, the pyridine-2,4-di-carboxylic acid crystallized as the monohydrate. After drying in vacuo at 115° C., 75 g (83.1 percent) of the anhydrous title product were obtained with a content of greater than 97 percent (HPLC).

The following examples were carried out analogously to Example 1a:

| Example | Starting Substance | Product | Yield |
|---|---|---|---|
| 2 | Pyridine-3,4-dicarboxylic acid | 2-Carbamoyl pyridine-4,5-dicarboxylic acid | 70 percent |
| 3 | 4-Methylpyridine | 4-Methylpyridine-2,6-dicarboxylamide | 81 percent |
| 4 | 4-Chloropyridine | 4-Chloropyridine-2-carboxamide | 55 percent |
| 5 | 2-Methyl-5-ethylpyridine | 6-Methyl-3-ethylpyridine-2-carboxyamide | 40 percent |
| 6 | 2,5-Dimethyl-pyrazine | 3,6-Dimethyl-2,5-pyrazine-dicarboxamide | 15 percent |
| 7 | 2-Methylquinoline | 2-Methyl-4-quinolinecarboxamide | 90 percent |
| 8 | 6-Methyl-2-pyridinecarbonitrile | 6-Cyano-2-methyl-3-pyridinecarboxamide | 25 percent |
| 9 | 6-Chloro-2-pyridinecarbonitrile | 6-Cyano-2-chloro-3-pyridinecarboxamide | 30 percent |

EXAMPLE 10

Process for the preparation of pyridine-2,4-dicarboxylic acid from isonicotinic acid 80 g (0.65 mol) of isonicotinic acid was suspended in 600 ml of acetonitrile at room temperature. 26 g (0.26 mol) of 98 percent strength sulfuric acid, 161 g (3.58 mol) of formamide and 42.4 g of water were then added. The suspension was heated to 70° C., after which 208.7 g (0.91 mol) of ammonium peroxodisulfate was added in portions such that the temperature did not exceed 75° C. After the mixture had been stirred at 73° C. for 90 minutes, 650 ml of water were added. Thereafter, the suspension was filtered and the filter cake was washed with 150 ml of water. The resultant 2-carbamoylpyridine-4-carboxylic acid was then suspended in 350 ml of water and the suspension was heated to 80° C. 208 g of 30 percent strength sodium hydroxide solution (1.56 mol) was then added in the course of 15 minutes. The mixture was then subsequently stirred until no further evolution of $NH_3$ was observed. The residual $NH_3$ was removed by heating the solution to 95° C.

After careful acidification of the solution to pH 1 with concentrated HCl and subsequent cooling, the title product crystallized out. The suspension was filtered at 5° C. The resultant product was then dissolved by being taking up again in 800 ml of boiling water and by subsequent acidification to pH 1 with concentrated HCl and recrystallized by subsequent cooling. After filtration, washing of the material on the filter with water and drying in vacuo, 81.5 (75 percent) of the title product was obtained with a content, according to HPLC, of >98 percent.

What is claimed is:

1. A process for the preparation of 2,4-pyridine dicarboxylic acid, comprising reacting 4-cyanopyridine or isonicotinic acid with formamide in the presence of peroxodisulfuric acid or a peroxodisulfate to provide a 2-carboxamide of said 4-cyanopyridine or said isonicotinic acid, respectively, and converting said 2-carboxamide of said 4-cyanopyridine or said isonicotinic acid by alkaline hydrolysis to 2,4-pyridine dicarboxylic acid.

2. The process according to claim 1 wherein the reaction is carried out in the presence of the peroxodisulfate.

3. The process according to claim 2 wherein ammonium peroxodisulfate is employed.

4. The process according to claim 3 wherein the peroxodisulfate is employed in the amount of 1.1 to 3.0 mol per mol of the 4-cyanopyridine or the isonicotinic acid employed.

5. The process according to claim 4 wherein the formamide is employed in an amount of 3 to 35 mol per mol of the 4-cyanopyridine or the isonicotinic acid employed.

6. The process according to claim 5 wherein the reaction is additionally carried out in the presence of a strong acid.

7. The process according to claim 6 wherein the strong acid is sulfuric acid.

8. The process according to claim 7 wherein the reaction is carried out at a temperature between 20° C. and 80° C.

9. The process according to claim 1 wherein the peroxodisulfuric acid or the peroxodisulfate is employed in the amount of 1.1 to 3.0 mol per mol of the 4-cyanopyridine or the isonicotinic acid employed.

10. The process according to claim 1 wherein the formamide is employed in an amount of 3 to 35 mol per mol of the 4-cyanopyridine or the isonicotinic acid employed.

11. The process according to claim 1 wherein the reaction is additionally carried out in the presence of a strong acid.

12. The process according to claim 11 wherein the strong acid sulfuric acid.

13. The process according to claim 1 wherein the reaction is carried out at a temperature between 20° C. and 80° C.

14. The process according to claim 1 wherein the reaction as carried out in the presence of the peroxodisulfuric acid.

15. The process according to claim 1 wherein the reaction is carried out in the presence of a polar inert solvent.

16. The process according to claim 1 wherein the reaction is conducted with 4-cyanopyridine.

17. The process according to claim 1 wherein the reaction is conducted with isonicotinic acid.

* * * * *